(12) United States Patent
Beckman et al.

(10) Patent No.: US 6,656,446 B1
(45) Date of Patent: Dec. 2, 2003

(54) SYNTHESIS OF HYDROGEN PEROXIDE

(75) Inventors: Eric J. Beckman, Pittsburgh, PA (US); Dan Hâncu, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/560,489

(22) Filed: Apr. 28, 2000

Related U.S. Application Data

(60) Provisional application No. 60/131,530, filed on Apr. 29, 1999.

(51) Int. Cl.[7] .......................................... C01B 15/026
(52) U.S. Cl. ...................................................... 423/591
(58) Field of Search .......................................... 423/591

(56) References Cited

U.S. PATENT DOCUMENTS

| | | | | |
|---|---|---|---|---|
| 5,268,160 A | * | 12/1993 | Albal et al. ................. | 423/591 |
| 5,968,472 A | * | 10/1999 | Oyague et al. .............. | 423/591 |
| 6,342,196 B2 | * | 1/2002 | Beckman et al. ........... | 423/588 |

* cited by examiner

*Primary Examiner*—Wayne A. Langel
(74) *Attorney, Agent, or Firm*—Bartony & Hare, LLP

(57) ABSTRACT

A method for synthesizing hydrogen peroxide comprises the step of: mixing an analog of a secondary alcohol that is soluble with carbon dioxide with a free radical initiator and oxygen in carbon dioxide to generate hydrogen peroxide. Another method of synthesizing hydrogen peroxide comprises the step of: mixing hydrogen, oxygen and a $CO_2$-philic catalyst in carbon dioxide phase. The $CO_2$-philic catalyst is soluble or miscible in carbon dioxide and is suitable to catalyze the reaction of hydrogen and oxygen to produce hydrogen peroxide. The method also comprises the step of reacting the hydrogen and oxygen to produce hydrogen peroxide.

23 Claims, 11 Drawing Sheets

Figure 1   Idealized asymmetric cloud point curve.

Figure 2  Effect of tail length on phase behavior of 2-AQ-NHCO-Kr:

(v) 2-AQ-NHCO-2500; (σ) 2-AQ-NHCO-5000

(λ) 2-AQ-NHCO-7500

Figure 3 Effect of tail length on phase behavior of 2-AQ-CH$_2$-OCO-Kr:

(σ) 2-AQ-CH$_2$-OCO-700; (λ) 2-AQ-CH$_2$-OCO-2500

(τ) 2-AQ-CH$_2$-OCO-5000; (ν) 2-AQ-CH$_2$-OCO-7500

Figure 4 Effect of head group on phase behavior:

(σ) 2-AQ-CH₂-OCO-5000; (τ) 2-AQ-N(Me)CO-5000

(λ) 1-AQ-NHCO-5000 (ν) 2-AQ-NHCO-5000

Figure 5 Effect of topology on phase behavior of Twin (2500)-AQ:

(τ) 1, 4-Twin (2500)-AQ; (σ) 1, 2 – Twin (2500)-AQ;

(λ) 2, 6 – Twin (2500)-AQ

Figure 6  Hydrogenation of 1.0 mM 2-AQ-NHCO-5000 in liquid $CO_2$ (P=3450Psi, T= 25 C) in the presence of powdered Pd (1%) / $Al_2O_3$ catalyst (3.14 g /l) monitored by UV spectroscopy.

SYNTHESIS OF HYDROGEN PEROXIDE

RELATED U.S. APPLICATION

U.S. Provisional Patent Application Ser. No. 60/131,530 filed Apr. 29, 1999, the disclosure of which is incorporated herein by reference.

FIELD OF THE INVENTION

The present invention relates to the synthesis of hydrogen peroxide, and more particularly, to the synthesis of hydrogen peroxide in which the use of organic solvents is reduced or eliminated.

BACKGROUND OF THE INVENTION

Hydrogen peroxide ($H_2O_2$) is often considered to be a "green" material, in that it is increasingly used to replace chlorine-containing reagents in paper bleaching and in water purification. For this reason, as well as others, hydrogen peroxide production is estimated to increase steadily through the beginning of the next century.

The production of hydrogen peroxide is a mature process in that the general procedure has not changed appreciably in twenty years. Indeed, recent research publications in the area of hydrogen peroxide synthesis are somewhat scarce. Typically, hydrogen peroxide is generated in a two-step process, wherein hydrogen is first reacted with a 2-alkyl anthraquinone (usually 2-ethyl or 2-amyl anthraquinone) in an organic solvent to produce the corresponding tetrahydroquinone (2-alkyl tetrahydroquinone) The reaction is catalyzed by a simple palladium-on-alumina catalyst. Conditions for this reaction are typically 30 to 70° C. with hydrogen pressures up to 300 psi. Given the nature of the reactants, the reactor contains three phases (gas, liquid, and solid catalyst) and previous work has shown that the reaction is completely mass transfer limited, such that the rate of the reaction is essentially the rate at which hydrogen diffuses into the liquid phase. Partly as a result of this inefficiency of hydrogen use, side reactions (hydrogenation of one or both of the aromatic rings) also occur, and byproducts build up during repeated cycling of the anthraquinone. These byproducts must periodically be removed and treated. The organic solvent employed is typically a mixture of an aromatic (a good solvent for the anthraquinone) and a long-chain alcohol (a good solvent for the hydroquinone).

The second step of the process involves oxidation of the hydroquinone, regenerating the anthraquinone and producing hydrogen peroxide. Here the catalyst is retained in the first reactor, and the solution of alkyl anthraquinone, alkyl tetrahydroquinone and organic solvent (the working solution) is transferred to the second reactor, where the hydroquinone is reacted with oxygen (as air or oxygen). This reaction is uncatalyzed. Similar to the first reaction, the second reaction is mass transfer limited by the rate at which oxygen can diffuse from the gas to liquid phases. Finally, the hydrogen peroxide is stripped from the organic solvent via liquid-liquid extraction with water and sold as an aqueous mixture (usually 30 to 50%).

Because the final step in the production of hydrogen peroxide involves a liquid-liquid extraction between aqueous and organic phases, the final product is contaminated to some extent by the organic phase. Given that $H_2O_2$ is promoted as a green reagent for paper production, and is also used in water purification, the organics in the final product must be minimized. Significant effort is thus made to strip the organic contaminants from the product.

Although approximately 95% of the world's hydrogen peroxide is produced via the anthraquinone process described above, a number of other synthetic routes exist. For example, from the 1960's to the 1980's, Shell maintained several hydrogen peroxide production plants that employed a free-radical initiated oxidation of a secondary alcohol (isopropanol) for the generation of hydrogen peroxide. These plants were closed, however, in the early 1980's because they could not compete economically with the well-known anthraquinone route to hydrogen peroxide production. The primary disadvantages to the use of secondary alcohol oxidation are that (a) one has to distill a complex mixture of hydrogen peroxide, water, residual alcohol, and the ketone byproduct of the reaction to purify the hydrogen peroxide product, and hot hydrogen peroxide is a safety hazard; and (b) the required reaction temperature for this process is rather high, 100 to 150° C., also a safety hazard. During the 1980's, Arco Chemical explored the use of another secondary alcohol, phenethyl alcohol, for use in the production of hydrogen peroxide. This secondary alcohol exhibited better reactivity than isopropanol, but that process suffers from similar disadvantages to the isopropanol process described above.

Arguably, the ideal synthetic route for producing hydrogen peroxide would be one that employs the simple reaction of hydrogen plus oxygen, yet which could also run safely. Clearly, a mixture of hydrogen and oxygen can pose a serious safety hazard, one fact that has prevented such a technology from being scaled up and commercialized to date. On the other hand, production of hydrogen peroxide from only oxygen and hydrogen would represent the most efficient (and thus the most inexpensive) and cleanest method by which to generate the product.

Indeed, a number of research groups throughout the world have been investigating a more direct route to the production of hydrogen peroxide, that is, via the direct reaction of hydrogen and oxidation. The keys to a successful process include (a) maintaining safe operating conditions, (that is, preventing explosion), (b) generating hydrogen peroxide continuously and at high rates (to satisfy economic constraints), and (c) preventing decomposition of the hydrogen peroxide product once it is formed. To date, attempts to develop a commercially viable synthetic route to hydrogen peroxide via the direct route of hydrogen and oxidation have met with very limited success.

It remains, therefore, very desirable to develop reactants and processes for the synthesis of hydrogen peroxide.

SUMMARY OF THE INVENTION

A method for synthesizing hydrogen peroxide using a $CO_2$-philic anthraquinone is described in U.S. patent application Ser. No. 09/106,480, filed Jun. 29, 1998, U.S. Pat. No. 6,342,196, and entitled SYNTHESIS OF HYDROGEN PEROXIDE, assigned to the assignee of the present invention, the disclosure of which is incorporated herein by reference. That method comprises generally the steps of:

synthesizing an analog of anthraquinone that is miscible with (in the case of a liquid analog) or soluble in (in the case of a solid analog) carbon dioxide;

reacting the analog of anthraquinone with hydrogen in carbon dioxide to produce a corresponding analog of tetrahydroquinone; and reacting the analog of tetrahydroquinone with oxygen to produce the hydrogen peroxide and regenerate the analog of anthraquinone.

Preferably, the regenerated analog of anthraquinone is recycled for future use.

The step of synthesizing an analog of anthraquinone that is miscible in carbon dioxide preferably comprises the step of attaching to anthraquinone at least one modifying or functional group that is relatively highly soluble in $CO_2$ ("$CO_2$-philic"). The miscibility/solubility of the resulting analogs of anthraquinone are several orders of magnitude greater at the operating pressures of the present invention than the solubility of 2-alkyl anthraquinone in carbon dioxide at pressures equal to or below 5000 psi. Alkyl-anthraquinones used in the commercial synthesis of hydrogen peroxide do not exhibit appreciable solubility in carbon dioxide at pressures below 5000 psi. In that regard, a number of studies have explored the solubility of alkyl-functional anthraquinones in carbon dioxide and found generally that the system exhibits solid-fluid phase behavior with maximum solubilities of approximately $10^{-2}$ mM. See, for example, Joung, S. N., Yoo, K. P., *J. Chem. Eng. Data*, 43, 9 (1998). Coutsikos, P., Magoulos, K., Tassios, D., *J. Chem. Eng. Data*, 42, 463 (1997). Swidersky, P., Tuma, D., Schneider, G. M., J., *Supercrit. Fl.*, 9, 12 (1996). ibid, 8, 100 (1995).

Preferably, the $CO_2$-philic functionalized anthraquinones and the corresponding hydroquinones exhibit reactivity similar to the 2-alkyl anthraquinone and hydroquinones used in the current commercial synthesis of hydrogen peroxide. Indeed, the kinetic rate constants calculated for the oxygenation of the functionalized anthraquinones were found to be approximately ten time greater than anthraquinone. The use of $CO_2$-philic groups to increase the solubility of a molecule in carbon dioxide is also discussed in U.S. Pat. No. 5,641,887, the disclosure of which is incorporated herein by reference.

In general, the analog of anthraquinone preferably has the formula:

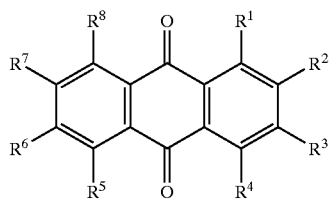

At least one of $R^1$, $R^2$, $R^3$, $R^4$, $R^5$, $R^6$, $R^7$, and $R^8$ (corresponding to the 1, 2, 3, 4, 5, 6, 7, and 8 carbons on the anthraquinone ring structure) is a modifying group or functional group that is miscible/soluble in carbon dioxide. Attachment of one or more such $CO_2$-philic groups to anthraquinone and other compounds results in an analog of anthraquinone and such other compounds that is miscible/soluble in carbon dioxide. In that regard, $R^1$, $R^2$, $R^3$, $R^4$, $R^5$, $R^6$, $R^7$, and $R^8$ are preferably, independently, the same or different, H, $R^C$ or $R^S R^C$, wherein $R^S$ is a connector or a spacer group and $R^C$ is a fluoroalkyl (fluorinated alkyl) group, a fluoroether (fluorinated ether) group, a silicone group, an alkylene oxide group, a phosphazene group or a fluorinated acrylate group. At least one of $R^1$, $R^2$, $R^3$, $R^4$, $R^5$, $R^6$, $R^7$, and $R^8$ is not H. Preferably, $R^C$ is a fluoroalkyl group, a fluoroether group or an alkylene oxide group. More preferably, $R^C$ is a fluoroether group or an alkylene oxide group.

The spacer group, $R^S$, when present, can simply be a connective group used to attach a $CO_2$-philic group to anthraquinone or can additionally act to space the $CO_2$-philic group away from the anthraquinone. The spacer group is preferably a group which provides a simple synthetic route to achieve the desired analog of anthraquinone without substantially adversely affecting the miscibility of the analog of anthraquinone in carbon dioxide or the reactivity of the analog of anthraquinone and the corresponding hydroquinone in the synthesis of hydrogen peroxide. For example, the spacer group can be an alkylene group, an amino group, an amido group, an ester group or an alkyl ester group. As used herein in connection with $R^S$, the term "alkylene group" refers to a linear or branched alkylene group. A linear alkylene group, for example, has the formula $-(CH_2)_n-$. As used herein in connection with $R^S$, the term "amino group" refers to a secondary amino group having the formula $-NH-$ or a tertiary amino group having the formula $-NR^{11}H-$, wherein $R^{11}$ can generally be any substituent that doesn't interfere with the reactivity of the desired analog. For example, $R^{11}$ can be an alkyl group. As used herein in connection with $R^S$, the term "amido group" refers to secondary amido having the formula $-NHCO-$, or a tertiary amido group having the formula $-NR^{11}CO-$ wherein $R^{11}$ is as defined above. As used herein in connection with $R^S$, the term "ester group" refers to a group having the formula $-OCO-$. As used herein in connection with $R^S$, the term "alkyl ester group" refers to a group having the formula $-R^{12}OCO-$, wherein $R^{12}$ is an alkyl group. The spacer group itself need not be $CO_2$-philic. If it is desired to use the spacer group to space the $CO_2$-philic group away from the anthraquinone ring structure, an alkylene group is preferably used, either alone or in combination with another connective group.

The total molecular weight of the $CO_2$-philic groups $R^C$ attached to the analog of anthraquinone is preferably between approximately 200 and approximately 7500 to make the analog of anthraquinone miscible/soluble in carbon dioxide. One or more $CO_2$-philic groups can be attached to the anthraquinone ring structure. For example, each of $R^2$, $R_3$, $R^6$, and $R^7$, can comprise a perfluoroalkyl group having a molecular weight of 50. More preferably, the total molecular weight of the $CO_2$-philic groups is between approximately 500 and approximately 5000. Most preferably, the total molecular weight of the $CO_2$-philic groups is between approximately 500 and approximately 1500.

The fluoroalkyl groups of the present invention are preferably linear perfluoroalkyl groups comprising the formula/repeat group:

wherein g is an integer.

The fluoroether groups of the present invention are preferably perfluorinated and comprise the formula/repeat group:

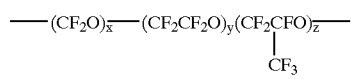

wherein each of x, y and z is an integer greater than or equal to 0 and at least one of x, y and z is not equal to 0.

The silicone groups of the present invention preferably comprise the formula/repeat group(s):

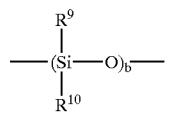

wherein $R^9$ and $R^{10}$ are chosen to not substantially affect the $CO_2$-philic nature of the silicone group or the reactivity of the functionalized analogs of anthraquinone. $R^9$ and $R^{10}$ may, for example, be, independently, the same or different, H, an alkyl group, an aryl group, an alkenyl group, or an alkoxyl group. In the above formula, b is an integer. Preferably, $R^9$ and/or $R^{10}$ is a fluoroalkyl group.

The alkylene oxide groups of the present invention preferably comprise the formula/repeat group:

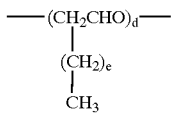

wherein d is an integer and e is an integer.

The fluorinated acrylate groups of the present invention preferably comprise the formula/repeat group:

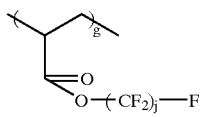

wherein g and j are integers.

The phosphazine groups of the present invention preferably comprise the formula/repeat group:

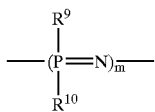

wherein m is an integer and $R^9$ and $R^{10}$ are as defined above.

The oxidation of the hydroquinone preferably takes place in carbon dioxide at substantially the same pressure as the hydrogenation reaction. The hydrogen peroxide product is preferably recovered via a liquid-liquid extraction between the carbon dioxide phase and an aqueous phase. The liquid-liquid extraction is preferably conducted without significantly reducing the operating pressure. Likewise, the carbon dioxide is preferably recycled to the extractor without a significant drop in pressure. Such a process for separation/recovery of hydrogen peroxide product avoids the high costs associated with recompression, while taking full advantage of carbon dioxide's green properties in running a contamination-free liquid-liquid extraction between a carbon dioxide phase and an aqueous phase.

Moreover, using carbon dioxide as the solvent for the process allows one to generate a single phase system of hydrogen plus anthraquinone (for the first reaction of the synthesis), or oxygen plus tetrahydroanthraquinone or tetrahydroquinone (for the second reaction of the synthesis). It is known that hydrogen is completely miscible with carbon dioxide above a temperature of approximately 31° C. Hydrogen and carbon dioxide have been found to not form separate phases under the operating conditions of the present invention. The reactions can thus be carried out without the mass transfer limitation of the current commercial process for the synthesis of hydrogen peroxide, suggesting that one could operate more efficiently, using less hydrogen and/or at lower temperatures, while producing fewer byproducts.

Furthermore, the operating pH for the stripping operation to recover the hydrogen peroxide from the organic phase into the aqueous stream in the current commercial process for the synthesis of hydrogen peroxide is preferably approximately 3.0 to partition the hydrogen peroxide into the aqueous phase. Because the carbon dioxide dissolves in water to form carbonic acid, the pH of the water in the presence of high pressure carbon dioxide is approximately 3.0, assisting in partitioning the hydrogen peroxide into the aqueous phase.

The present inventors have discovered that synthetic routes to the production of hydrogen peroxide other than via $CO_2$-philic anthraquinone can be modified to take place in a carbon dioxide phase. For example, the present invention provides a method for synthesizing hydrogen peroxide, comprising generally the step of mixing an analog of a secondary alcohol that is miscible with or soluble in carbon dioxide with a free radical initiator and oxygen in carbon dioxide (preferably liquid or supercritical carbon dioxide) to generate hydrogen peroxide. The free radical initiator may, for example be a peroxide. Preferably, the free radical initiator is hydrogen peroxide. The free radical initiator is preferably present in an amount less than approximately 1 wt % of the analog of the secondary alcohol. The reaction preferably takes place in a pressure range of approximately 900 psi to approximately 2500 psi. The reaction also preferably takes place in a temperature range of approximately 20° C. to approximately 100° C.

The analog of a secondary alcohol may, for example, have the formula:

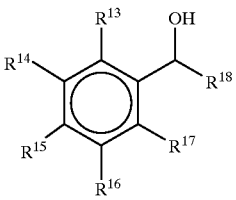

wherein $R^{13}$, $R^{14}$, $R^{15}$, $R^{16}$, and $R^{17}$ are independently, the same or different, H, $R^C$ or $R^S R^C$, wherein $R^S$ is a spacer group and $R^C$ is a $CO_2$-philic group, and wherein at least one of $R^{13}$, $R^{14}$, $R^{15}$, $R^{16}$, and $R^{17}$ is not H, and $R^{18}$ is an alkyl group (for example, a methyl group). Two or more $CO_2$-philic groups can be present. The $CO_2$-philic groups and spacer groups are generally as described above. The $CO_2$-philic groups preferably comprise a fluoroalkyl group, a fluoroether group, a silicone group, an alkylene oxide group, a fluorinated acrylate group, or a phosphazine group. As also described above, the spacer group may be an alkylene group, an amino group, an amido group, an alkyl ester group or an ester group. For example, the spacer group may be —NHCO—, —NCH$_2$CO— or —CH$_2$OCO—.

Preferably $R^{13}$ and $R^{15}$ are H in the above compound. Limiting the $CO_2$-philic substituents to the 3 and 5 position on the aromatic ring (that is, $R^{14}$ and $R^{16}$) is preferred for minimization of byproduct formation during hydrogenation.

The secondary alcohol may also have the formula $R^{11}$CH(OH)$R^{18}$ wherein $R^{11}$ is a $CO_2$-philic group and $R^{18}$ is an alkyl group (for example a methyl group). Aromatic secondary alcohols typically exhibit greater reactivity, however.

The method preferably also comprises the step of regenerating the analog of the secondary alcohol by hydrogenating the corresponding $CO_2$-philic ketone produced in the reaction. For example, the $CO_2$-philic ketone may be cycled to a hydrogenation reactor where the secondary alcohol is regenerated.

The reaction of the analog of the secondary alcohol with the free radical initiator and oxygen may take place in the presence of a catalyst. A catalyst is not necessary, however. Preferably, a catalyst, when present, is miscible in or soluble in carbon dioxide. The catalyst may, for example, have the formula:

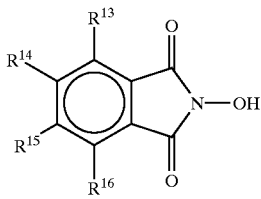

wherein $R^{13}$, $R^{14}$, $R^{15}$ and $R^{16}$, are independently, the same or different, H, $R^C$ or $R^S R^C$, wherein $R^S$ is a spacer group and $R^C$ is a $CO_2$-philic group as described above. Although not necessary, the catalyst is preferably $CO_2$-philic. Therefore, at least one of $R^{13}$, $R^{14}$, $R^{15}$ and $R^{16}$ is preferably not H. Two or more $CO_2$-philic groups may be present. In the case that the catalyst is not $CO_2$-philic, the catalyst will be heterogeneous. Use of a heterogeneous catalyst may facilitate keeping the catalyst in the oxidation reactor.

The present invention also provides a chemical compound having the formula:

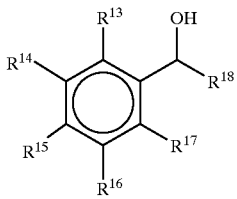

wherein $R^{13}$, $R^{14}$, $R^{15}$, $R^{16}$, $R^{17}$ and $R^{18}$ are as described above.

The present invention also provides a compound having the formula:

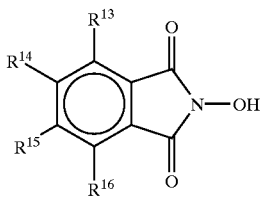

wherein $R^{13}$, $R^{14}$, $R^{15}$ and $R^{16}$ are as described above.

Still further, the present invention provides a compound having the formula $R^{13}CH(OH)R^{18}$ wherein $R^{13}$ and $R^{18}$ are as described above.

The present invention also provides a method for synthesizing hydrogen peroxide, comprising the steps of:

mixing hydrogen, oxygen and a $CO_2$-philic catalyst in carbon dioxide (preferably liquid or supercritical carbon dioxide), the $CO_2$-philic catalyst being soluble or miscible in carbon dioxide and being suitable to catalyze the reaction of hydrogen and oxygen (in the carbon dioxide phase) to produce hydrogen peroxide; and reacting hydrogen and oxygen to produce hydrogen peroxide. The method preferably further comprises the step of extracting the hydrogen peroxide product into an aqueous phase.

The method may also comprise the step of creating a second phase, which is an aqueous phase, in contact with the carbon dioxide phase to create a biphasic system. In this embodiment, the hydrogen peroxide product preferentially partitions into the aqueous phase.

The reaction preferably takes place in a pressure range of approximately 900 psi to approximately 2500 psi. The reaction also preferably takes place in a temperature range of approximately 20° C. to approximately 100° C.

The $CO_2$-philic catalyst may have the formulas $M(L)_r X_t$, wherein M is a group 8, 9 or 10 metal, L is a $CO_2$-philic ligand, X is a halogen, r is an integer between 1 and 3 and t is an integer between 1 and 2. Preferably, M is Pd. L may, for example, be $P(R^C-C_6H_4)_3$ or $P(R^C R^{19})_3$, wherein $R^{19}$ is an alkyl group and wherein $R^C$ is a $CO_2$-philic group as described above. $R^C$ may, for example, be 1H, 1H, 2H, 2H-perfluorooctyl(—$(CH_2)_2(CF_2)_6F$). Preferably, X is Cl.

As discussed above, the $CO_2$-philic analog compounds of the present invention are typically several orders of magnitude more soluble in or miscible with carbon dioxide than the corresponding underivitized compounds, while retaining their reactivity.

DETAILED DESCRIPTION OF THE INVENTION

Figure 1:
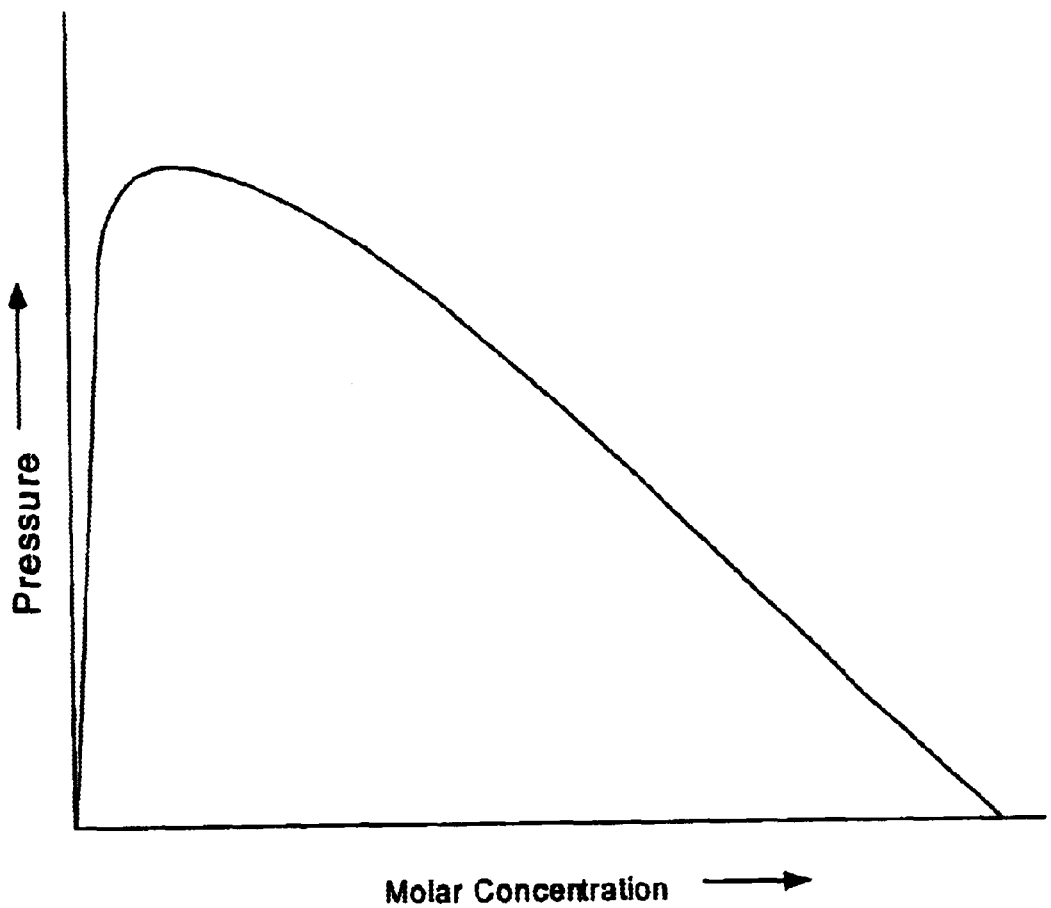
FIG. 1 illustrates an asymmetric cloud point curve for a functionalized anthraquinone-carbon dioxide system.

Carbon dioxide has received significant scientific interest over the past 15 years because it is considered a "green" alternative to conventional organic solvents. Carbon dioxide is inexpensive (approximately $80/ton, 1–2 orders of magnitude less than conventional solvents), non-flammable, not currently regulated as a volatile organic chemical by the U.S. EPA, and not regulated by the U.S. FDA in food or pharmaceutical applications. The latter advantage has lead to the commercialization of several large (greater than 50 million pounds per year) food processing ventures using carbon dioxide.

Carbon dioxide's inherent "green" properties make it particularly desirable for use in liquid-liquid extraction from water. While any organic solvent will contaminate water to a certain degree in a liquid-liquid extraction, in the case carbon dioxide this "contamination" obviously does not require remediation. Moreover, use of carbon dioxide as a solvent in conjunction with gaseous reactants can eliminate certain transport limitations to reaction.

Although carbon dioxide possesses distinct advantages as a solvent, it also exhibits a number of disadvantages which have limited commercial applications, for the most part, to food processing and polymer foam production. First, use of carbon dioxide (in either the liquid or supercritical state) requires the use of elevated pressures (the vapor pressure of carbon dioxide at room temperature is over 900 psi). Consequently, design and construction of equipment is significantly more expensive than for analogous processes carried out at atmospheric pressure.

Second, utility costs resulting from processing with high pressure carbon dioxide can be prohibitively high. For example, while it has been suggested that depressurization of a carbon dioxide solution to one atmosphere is an easy route to recovery of products, a carbon dioxide-based process may not be economically viable if extensive depressurization is used to recover dissolved products. Indeed, the known carbon dioxide-based coffee decaffeination process is economically viable, in part, because the carbon dioxide is not depressurized to recover the caffeine following stripping of caffeine from the coffee beans. That process uses water to extract the caffeine from the carbon dioxide in a countercurrent liquid-liquid column (the caffeine is ultimately recovered via reverse osmosis).

Another significant obstacle to the use of carbon dioxide as a solvent in conventional chemical processes is its low solvent power. Although carbon dioxide's solvent power was once suggested to be comparable to that of liquid alkanes, recent research has shown that this generalization is in error. Calculated solubility parameters for carbon dioxide are approximately 4–5 cal/cm$^3$ in the liquid state, similar to that of fluorinated materials and slightly lower than that for silicones. It is generally accepted that carbon dioxide will not solubilize significant quantities of polar, high molecular weight, or ionic compounds. Low solubilities of compounds of interest require large volumes of carbon dioxide in a potential process, and thus the chance for favorable economics diminishes.

Synthesis of $CO_2$-Miscible Functionalizes Anthraquinones (FAQ'S)

In the synthesis of hydrogen peroxide via $co_2$-miscible functionalized anthraquinones, novel, highly $CO_2$-miscible/ soluble analogs of 2-alkyl anthraquinones are first synthesized. These functionalized analogs are then use in the synthesis of hydrogen peroxide in carbon dioxide via sequential reaction with hydrogen, and then oxygen as illustrated below.

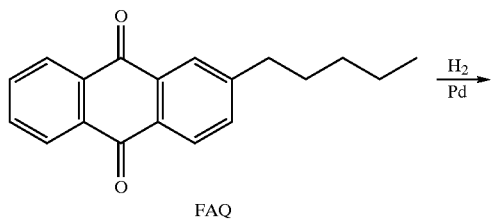

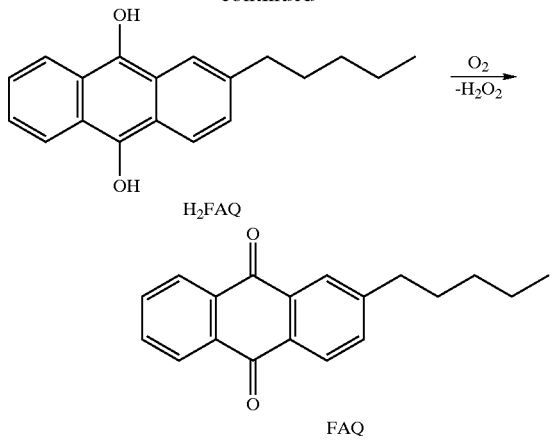

2-alkyl anthraquinones typically used in the commercial synthesis of hydrogen peroxide exhibit negligible solubility in carbon dioxide at pressures up to 5000 psi at room temperature. It has been discovered that highly $CO_2$-soluble/ miscible analogs of anthraquinone can be synthesized via modification or functionalization of anthraquinone with $CO_2$-philic groups. Such functionalized anthraquinones are often abbreviated as FAQ's herein. $CO_2$-philic groups suitable for use in the reactions include, for example, fluoroether groups, fluoroalkyl groups, silicones, fluorinated acrylates and phosphazines.

Analogs of 2-alkyl anthraquinone have been synthesized via the reaction of a commercially available anthraquinone functionalized with a first reactive group with a $CO_2$-philic group functionalized with a second reactive group, wherein the first reactive group and the second reactive group are selected to react to link the $CO_2$-philic group to the anthraquinone ring structure via a resultant connector or spacer group $R^S$. The $CO_2$-philic group can also be directly linked to the anthraquinone ring structure. Oligomeric (generally, with a molecular weight above 50) fluoroether $CO_2$-philic groups were used as models in several studies. For example, fluoroether acid chloride (generated from a 2500 molecular weight (MW) fluoroether carboxylic acid obtained from Dupont) was reacted with 2-amino anthraquinone (obtained from Aldrich Chemical). In that reaction, the acid chloride functional group and the amino functional group react to form an amide connector or linkage.

The functionalized fluoroether anthraquinone analogs are much more soluble in carbon dioxide than a 2-alkyl anthraquinone. Moreover, the $CO_2$-miscible/soluble analogs of anthraquinone were found to retain their reactivity towards hydrogen.

Phase Behavior of Functionalized Anthraquinones

Mixtures of the FAQ analogs and carbon dioxide were found to exhibit asymmetric liquid-liquid phase envelopes in P-x space. An idealized representation of such an asymmetric liquid-liquid phase envelope is illustrated in FIG. 1. To achieve complete miscibility over a broad range of concentrations, the operating pressure is preferably chosen to be above the maximum of the cloud point curve. However, the reactions are preferably operated at room temperature and at as low a pressure as possible to reduce operating costs. Phase behavior studies of a number of fluoroether model FAQ's were thus undertaken to study the effect of various parameters on the miscibility of the FAQ analogs in carbon dioxide.

In that regard, the effects of three different parameters on solubility of the FAQ analogs in carbon dioxide have been studied: (1) the effect of tail length, (2) the effect of head group, (3) the effect of numbers of tails and the position of the tail on the anthraquinone aromatic rings.

Figure 2:
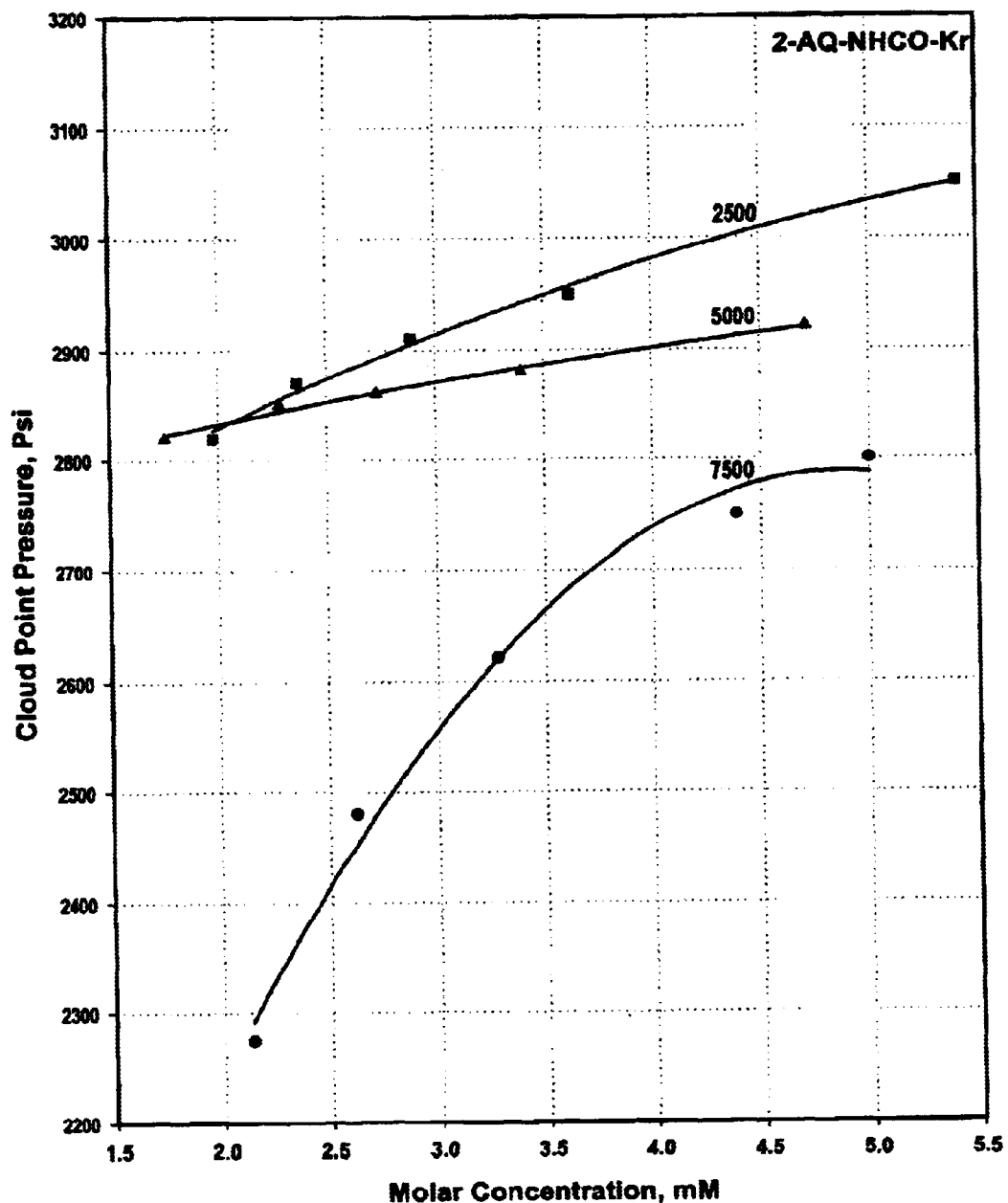
FIG. 2 illustrates the effect of functional group length upon the phase behavior of an analog of anthraquinone.
Figure 3:
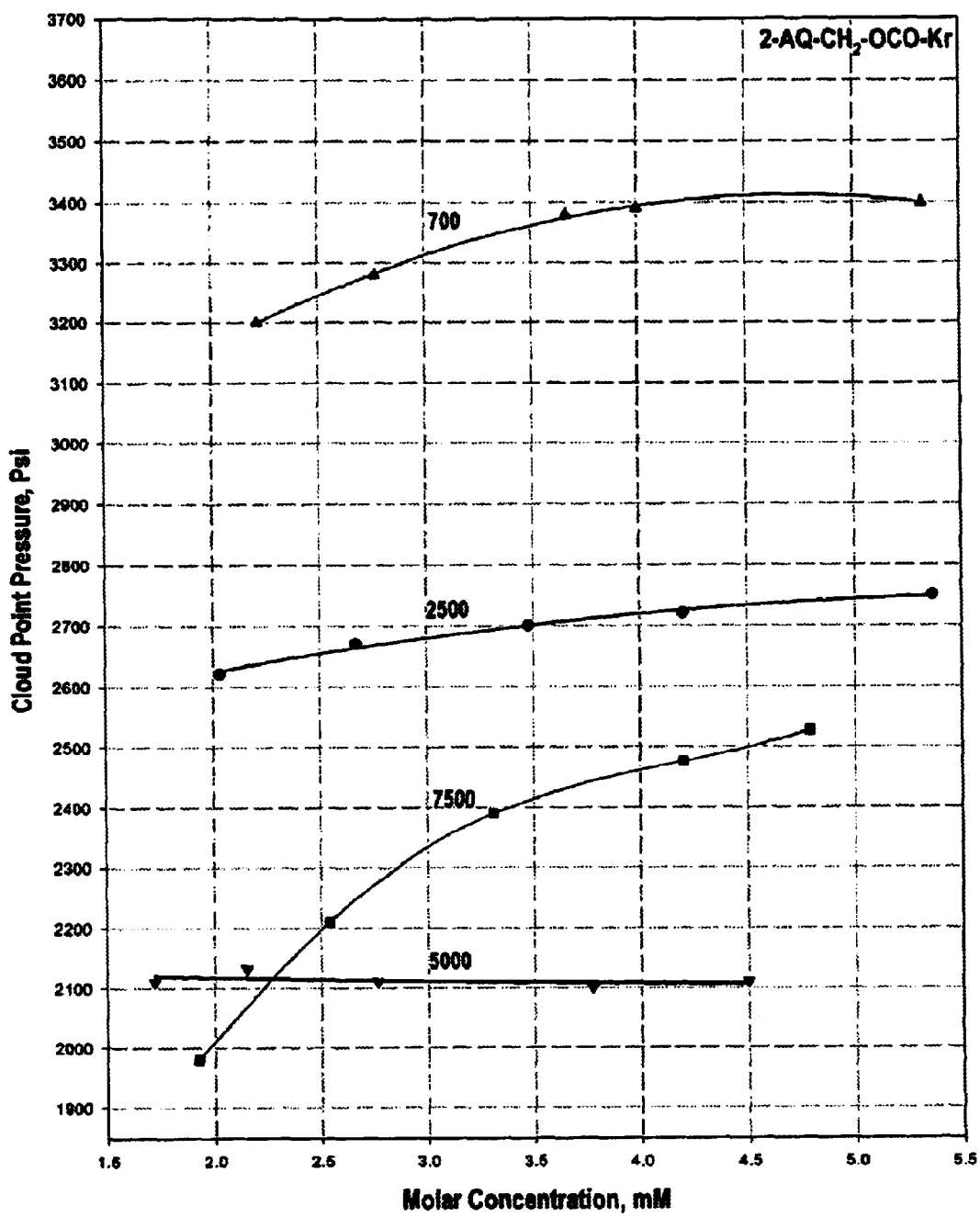
FIG. 3 illustrates the effect of functional group length upon the phase behavior of another analog of anthraquinone.

FIGS. 2 and 3 depict a portion of the cloud point curves of a number of FAQ's having different tail lengths. In FIG. 2, the effect of tail length (MW=2500, 5000 and 7500) upon the miscibility in carbon dioxide of a fluoroether oligomer attached to the 2-carbon of the anthraquinone ring by an amide connector group is illustrated. In FIG. 3, the effect of tail length (MW=700, 2500, 5000 and 7500) upon the miscibility in carbon dioxide of a fluoroether oligomer attached to the 2-carbon of the anthraquinone ring by an ester connector group is illustrated. As illustrated in FIGS. 2 and 3, the pressure required to achieve miscibility generally reduces with increasing tail length. However, as illustrated in a comparison of the cloud point curves of the 5000 and 7500 MW analogs in FIG. 3, as tail length (MW) increases, the gain in solubility due to a higher contribution of the hydrophobic/$CO_2$-philic group ($R^C$) is eventually overcome by the larger value of the entropy of mixing. At this point, the global effect of these two factors is a decrease in solubility compared to lower molecular weigh tails.

Figure 4:
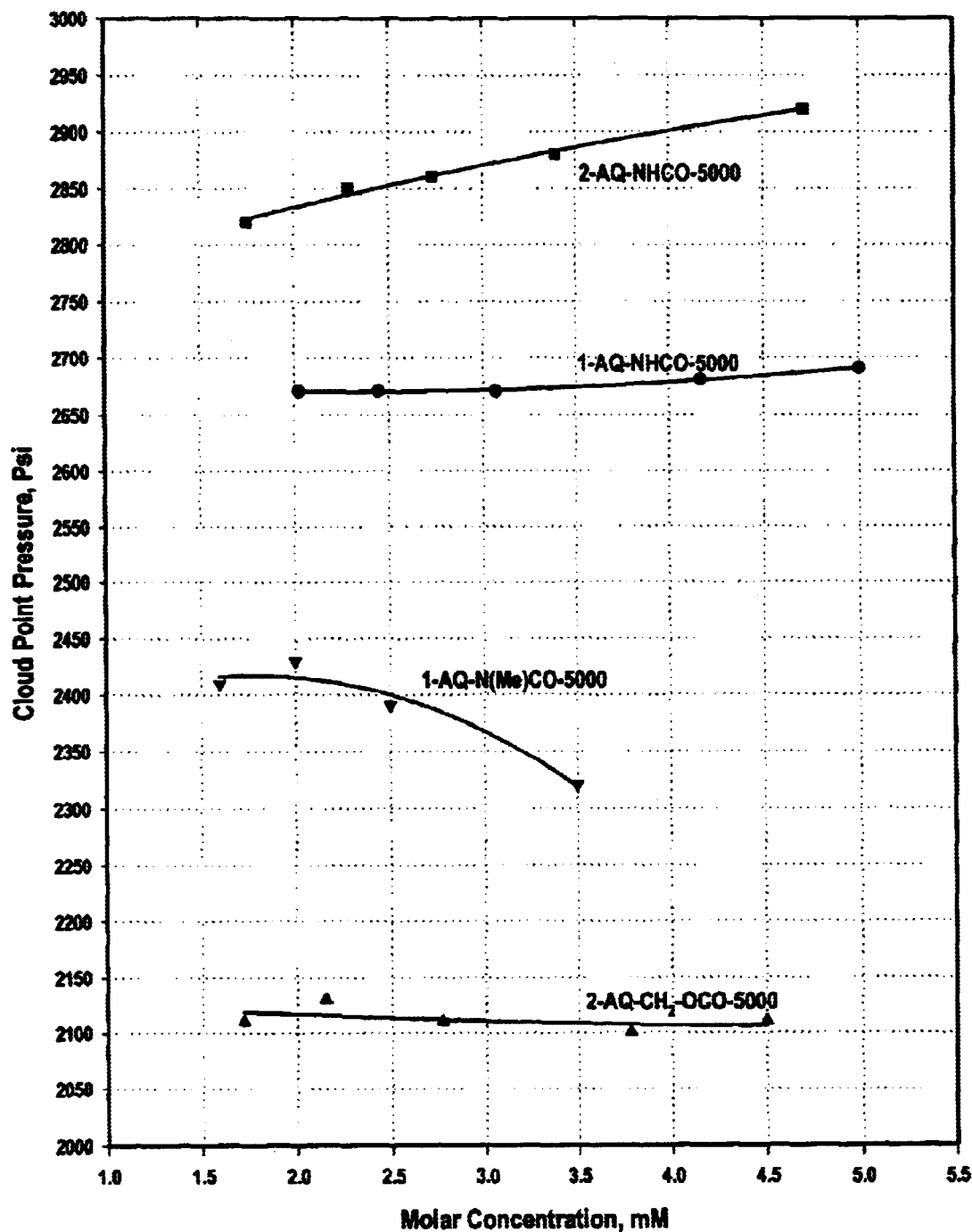
FIG. 4 illustrates the effect of the identity of a spacer group and the position of the functional group upon the phase behavior of an analog of anthraquinone.

In the studies of FIG. 4, the effect of the identity of the connector or spacer group ($R^S$) and the position thereof upon the miscibility of the FAQ is illustrated. As illustrated, the miscibility of the FAQ with the ester spacer group is greater than those with the amide linkage. This phenomenon is believed to result from the ability of certain spacer groups to hydrogen bond, and thus resist salvation by carbon dioxide. Such hydrogen bonding does not occur in the case of the methyl ester spacer group (shown below) of FIG. 4.

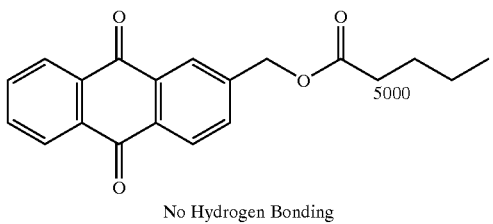

No Hydrogen Bonding

Likewise, hydrogen bonding does not occur in the case of a tertiary amide spacer groups such as an —NCH$_2$CO— (shown below).

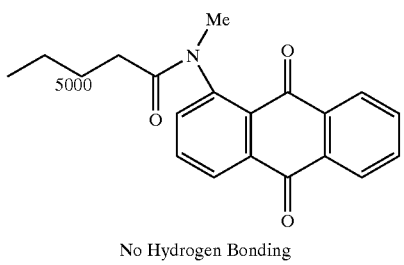

No Hydrogen Bonding

In general, replacement of the secondary amide proton with a methyl group is found to drop the cloud point curve by approximately 700 psi. Replacement of the tertiary amide spacer with an ester spacer drops the cloud point curve approximately an additional 200 psi, revealing a thermodynamic preference of carbon dioxide for the 2-methyl ester linkage over the N-substituted amide.

Figure 5:
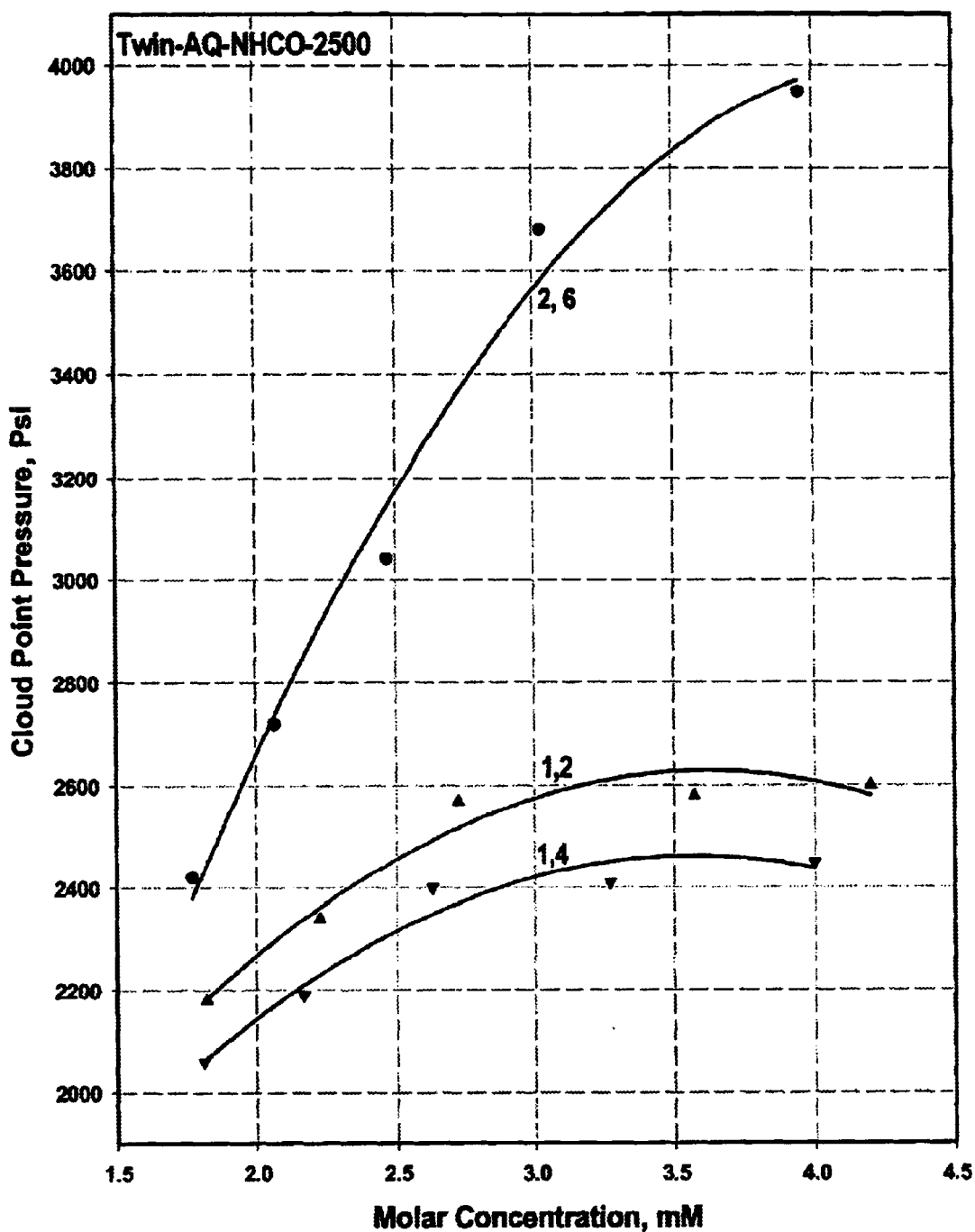
FIG. 5 illustrates the effect of the position of the functional groups upon the phase behavior of a difunctionalized analog of anthraquinone.
Figure 6:
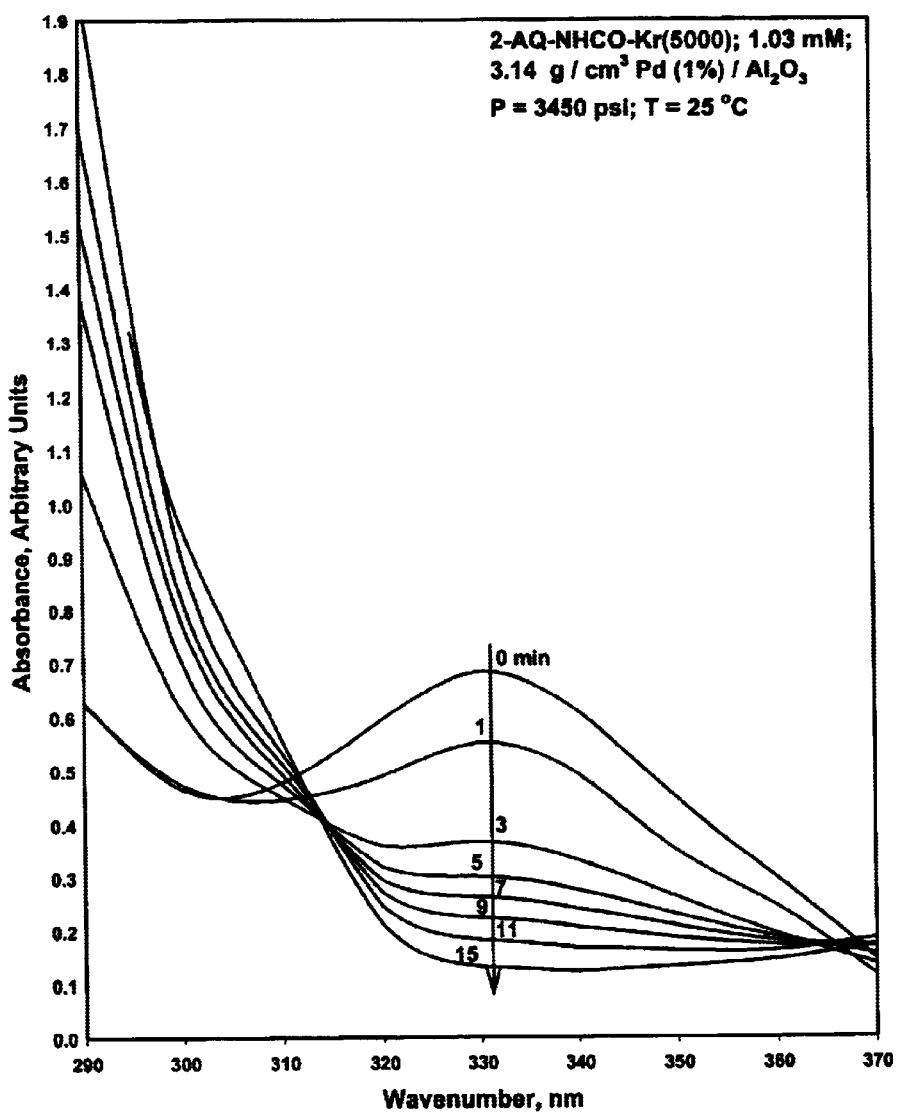
FIG. 6 illustrates the hydrogenation of an analog of anthraquinone as monitored by UV spectroscopy.

Furthermore, the position of spacer groups capable of forming hydrogen bonds also affects the miscibility of the FAQ. As illustrated in FIGS. 4 and 5 and in the chemical formulas below, 1-, 1, 4- and 1, 2- substitutions, which can readily form intramolecular hydrogen bonds, exhibit greater miscibility than 2-, and 2, 6- substitutions, which can only form intermolecular hydrogen bonds.

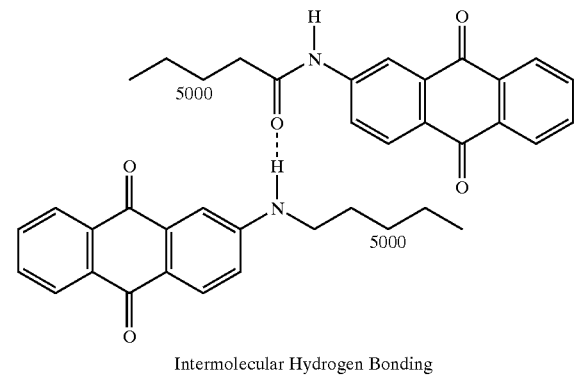

Intermolecular Hydrogen Bonding

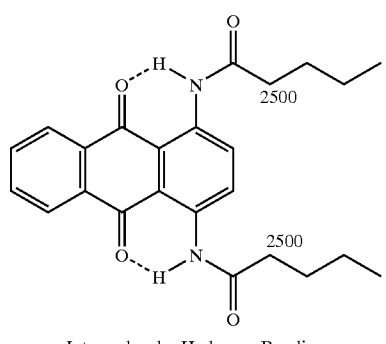

Intramolecular Hydrogen Bonding

Rate of Reaction/Diffusion Coefficients

In a heterogeneous catalytic system as occurs in the hydrogenation reaction, the overall rate of reaction can be controlled or limited either by the inherent kinetics of the reaction or by the rate of diffusion of one or more of the reactants to the catalytic sites. The effectiveness factor, or $\eta$, is the ratio of the actual rate to that of the purely kinetic rate, such that an effectiveness factor of 1.0 indicates a purely kinetically controlled reaction, while lower values imply mass transport limitations. The effectiveness factor is a strong function of the Thiele modulus (a dimensionless number incorporating both the true kinetic rate constant and the diffusion coefficient for the reactants within the catalyst particle). As the diffusion coefficient increases, the Thiele modulus decreases and the effectiveness factor approaches 1.0.

Figure 7:
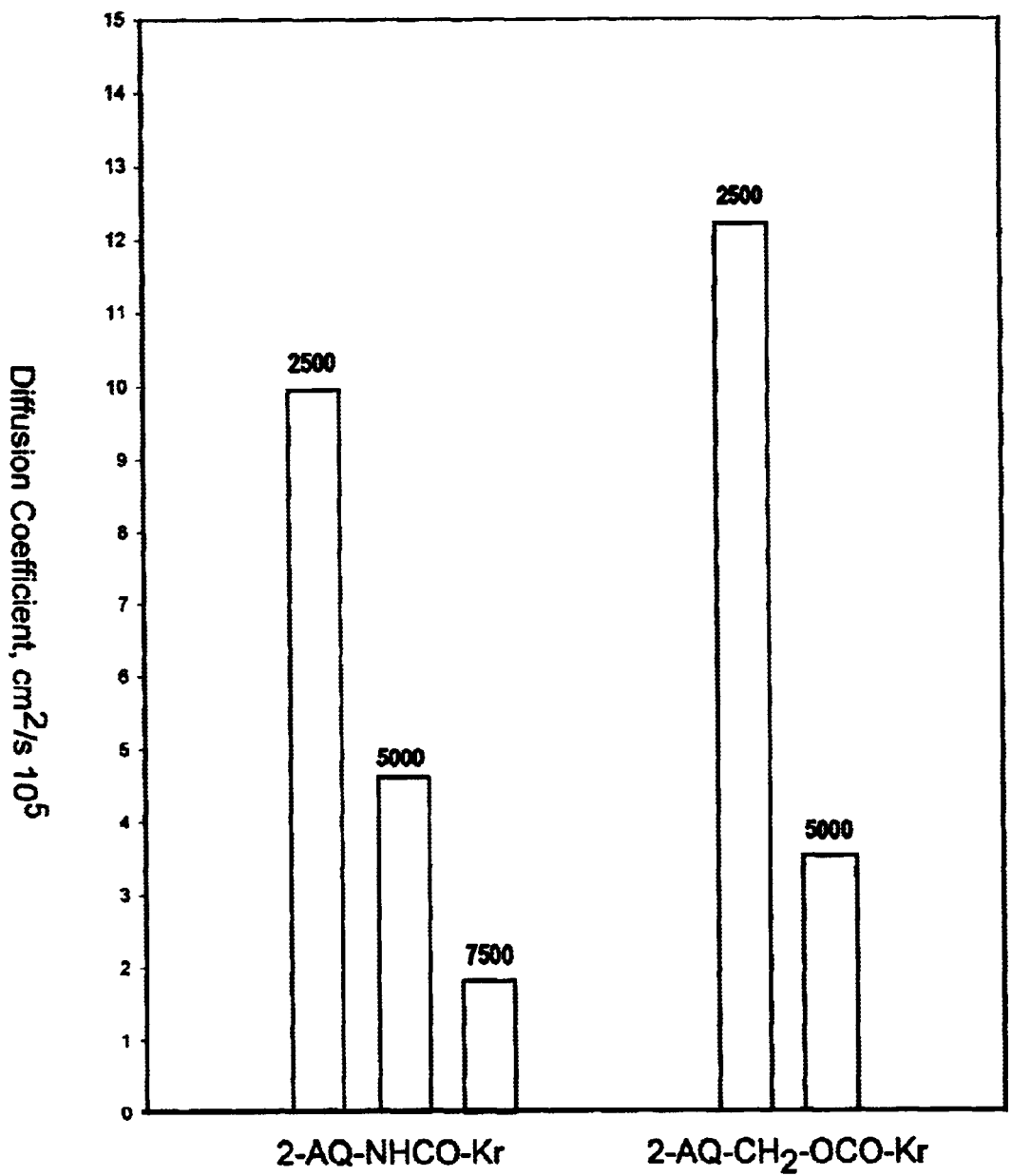
FIG. 7 illustrates the effect of the length of molecular weight of the $CO_2$-philic functional group upon the diffusion coefficient.
Figure 8:
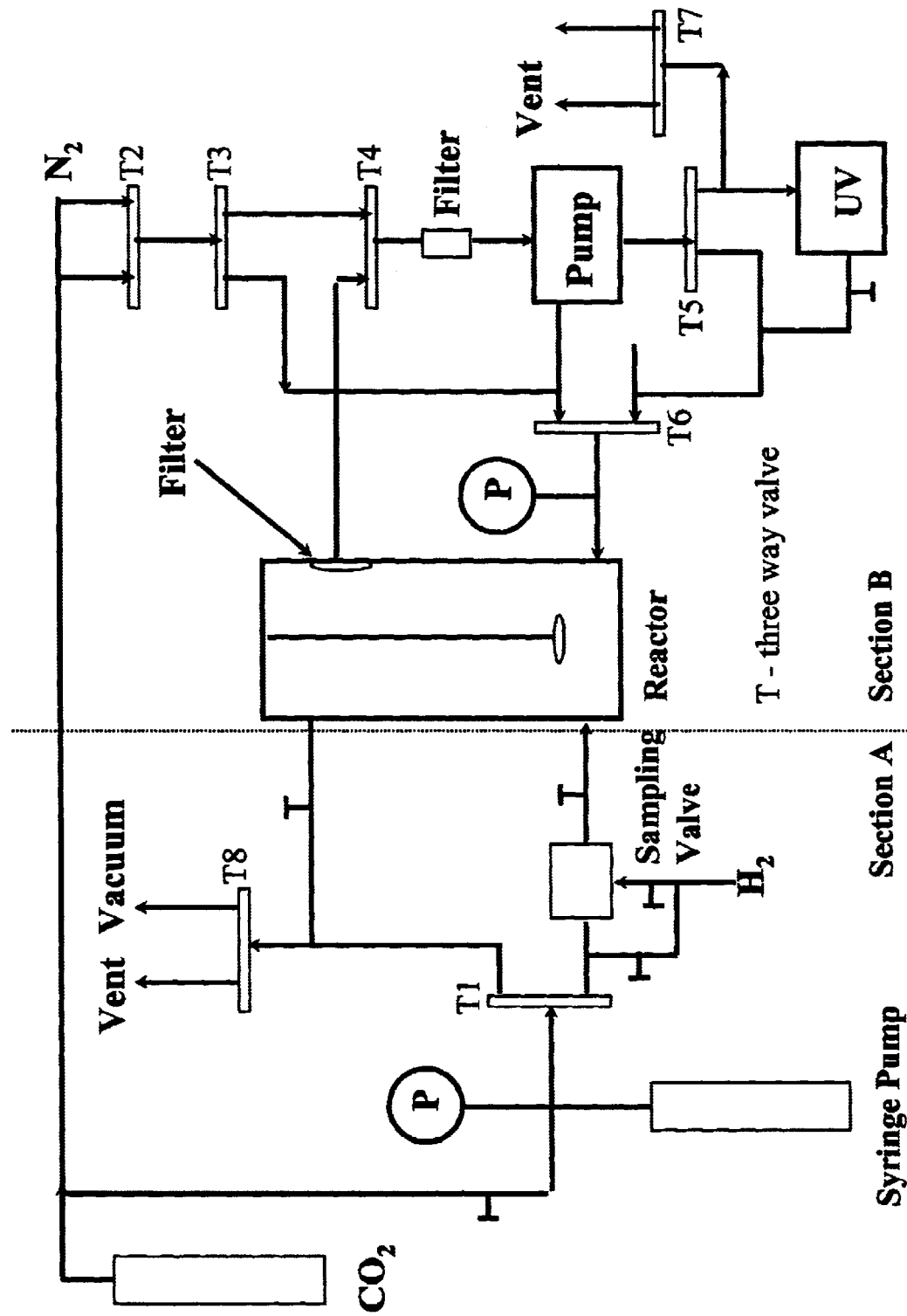
FIG. 8 illustrates one embodiment of a reactor system of the present invention.

In several studies, effective pseudo-first order rate constants, $k_{eff}$, (including contributions from both the true kinetic rate constant and the diffusion coefficient of the functionalized analog of anthraquinone in the pores of the catalyst) were studied for the hydrogenation reaction. The calculated kinetic data and diffusion coefficients for functional groups of different lengths and spacer groups are set forth in Table 2 and in FIG. 7. As illustrated, the diffusion coefficient was found to decrease with increasing functional group length.

Synthesis of Hydrogen Peroxide from $CO_2$-Philic Secondary Alcohols

Figure 9:
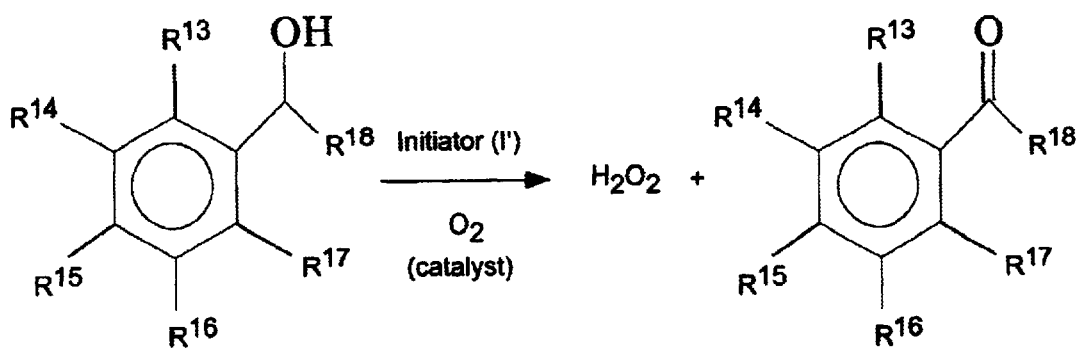
FIG. 9 illustrates an embodiment of the reaction of an $CO_2$-philic secondary alcohol in carbon dioxide to produce hydrogen peroxide.

In this method, hydrogen peroxide is synthesized via a free-radically initiated oxidation of a $CO_2$-philic analog of a secondary alcohol (for example a $CO_2$-philic derivitized phenethyl alcohol) in carbon dioxide, with liquid-liquid extraction into water used to recover the product. One embodiment of this method is illustrated in FIG. 9. The corresponding $CO_2$-philic ketone (illustrated, for example, in FIG. 9) produced during the reaction is preferably cycled to a hydrogenation reactor where the secondary alcohol can be regenerated. For example, the $CO_2$-philic ketone byproduct may be routed to a hydrogenation reactor wherein the secondary alcohol is regenerated over a palladium or other suitable catalyst. Furthermore, a derivitized (that is, $CO_2$-philic modified; to allow $CO_2$ solubility or miscibility) catalyst such as derivitized N-hydroxy phthalimide catalyst may be used to lower the required reaction temperature.

$CO_2$-philic secondary alcohols for use in the present invention can be synthesized by reduction of the commercially available compound 3,5 bistrifluoromethyl phenylmethylketone to the corresponding alcohol. Other suitable $CO_2$-philic secondary alcohols can be readily synthesized from commercially available 3,5 bisiodo phenylmethylketone.

The method of the present invention provides a number of important advantages over prior methods in which secondary alcohols were used in the synthesis of hydrogen peroxide, including, for example:

1. The separation of hydrogen peroxide from the reaction mixture is eased because the alcohol and the ketone byproduct are each soluble only in carbon dioxide, and the hydrogen peroxide partitions preferentially to the aqueous phase.
2. Oxygen is miscible with carbon dioxide, thus eliminating mass transfer limitations present in current processes.
3. The use of a $CO_2$-philic catalyst should lower the required reaction temperature.
4. The attachment of the $CO_2$-philic groups to the secondary alcohol will not only allow solubility in carbon dioxide, but will also prevent hydrogenation (via steric hindrance) of the aromatic ring and thus prevent deactivation of the alcohol.

As discussed above, the reaction temperature of the analog of the secondary alcohol with the free radical initiator and oxygen may be decreased in the presence of a catalyst. Preferably, the catalyst is miscible in or soluble in carbon dioxide. The catalyst may, for example, have the formula:

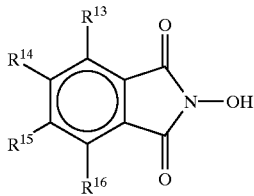

wherein $R^{13}$, $R^{14}$, $R^{15}$ and $R^{16}$ are as described above.

Direct Synthesis of Hydrogen Peroxike from Hydrogen and Oxygen

Figure 10:
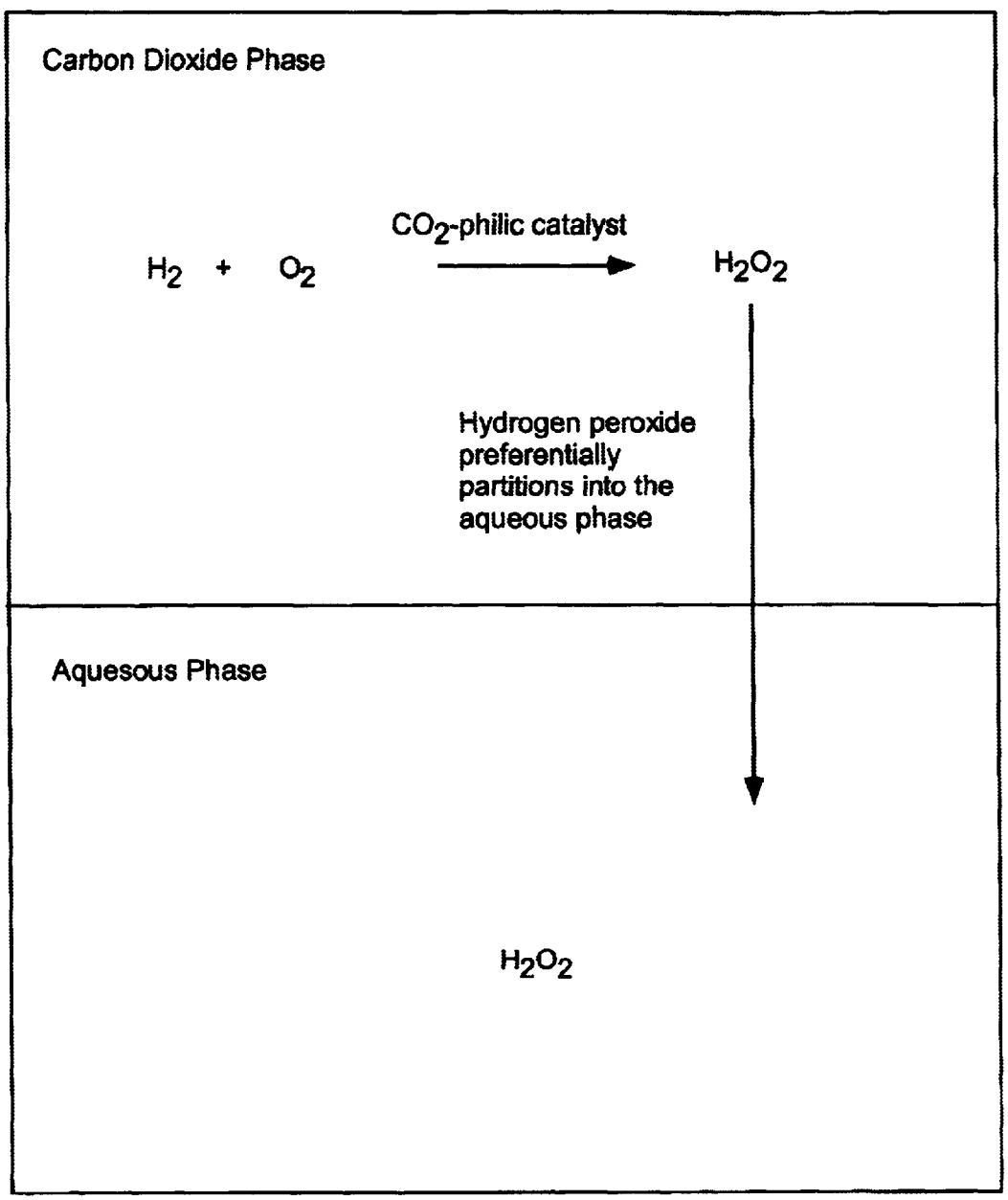
FIG. 10 illustrates a reaction scheme for the synthesis of hydrogen peroxide from hydrogen and oxygen in carbon dioxide using a $CO_2$-philic catalyst.
Figure 11:
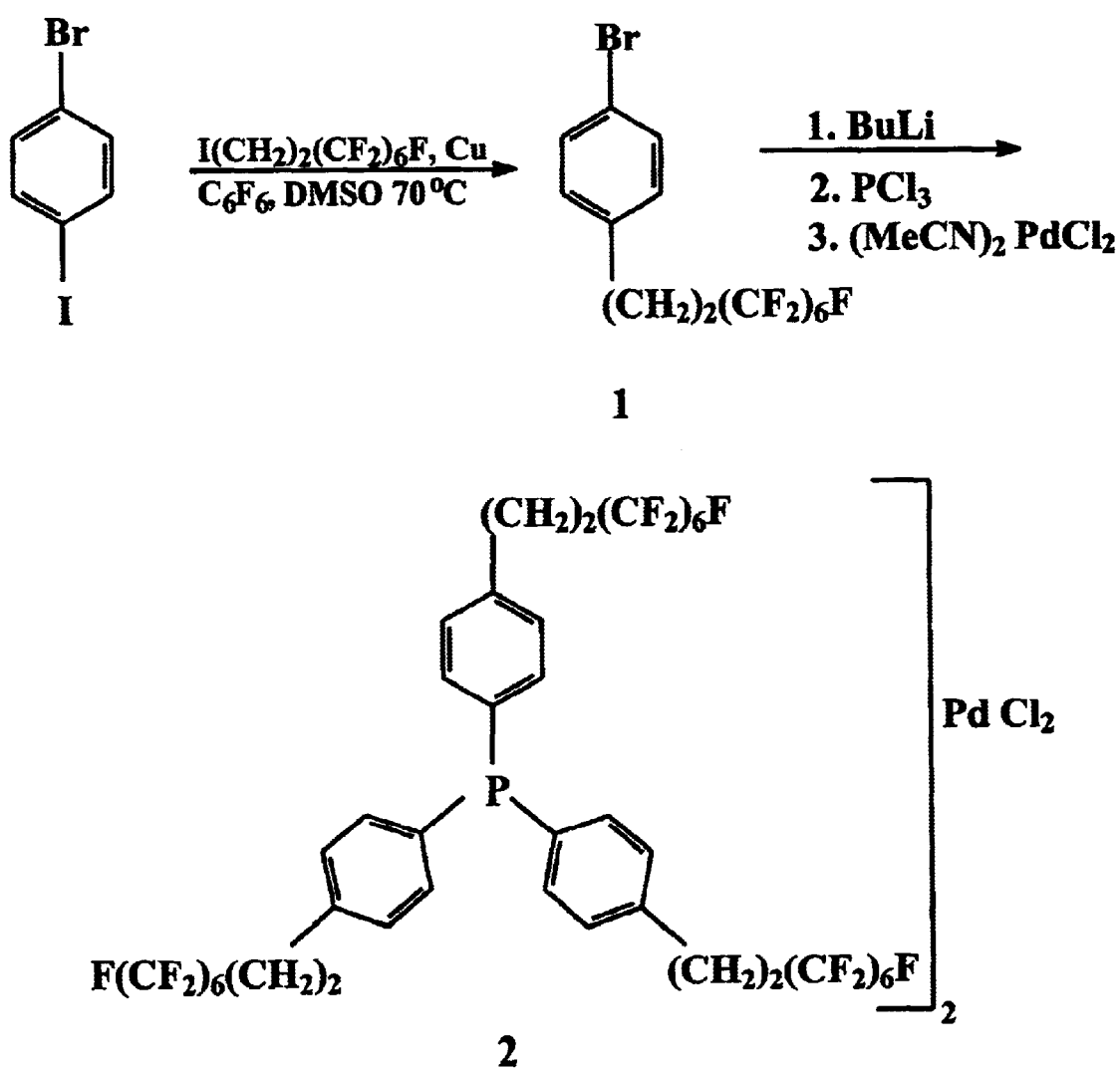
FIG. 11 illustrates an embodiment of an experimental apparatus for the direct synthesis of $H_2O_2$ from hydrogen and oxygen in $CO_2$.

In this method of the present invention, hydrogen peroxide is produced from hydrogen and oxygen wherein liquid or supercritical carbon dioxide is used as a reaction media as illustrated in FIG. 10. An apparatus for carrying but the reaction is illustrated in FIG. 11. The process is preferably conducted in a bi-phasic liquid system consisting of: (1) a carbon dioxide phase containing dissolved $H_2$, $O_2$ and a $CO_2$-philic (that is, relatively highly soluble or miscible in carbon dioxide) catalyst and (2) an aqueous phase. Hydrogen peroxide is formed in carbon dioxide phase followed by partition or extraction into an aqueous phase. Preferably, the $CO_2$-philic catalyst has a solubility of at least 0.5 millimolar at a pressure of 3500 psi at 25°. More preferably, the $CO_2$-philic catalyst has a solubility of at least 5.0 millimolar at a pressure of 1500 psi at 25°.

The $CO_2$-philic catalyst may have the formulas $M(L)_rX_t$, wherein M is a group 8, 9 or 10 metal, L is a $CO_2$-philic ligand, X is a halogen, r is an integer between 1 and 3 and t is an integer between 1 and 2. Preferably, M is Pd. L may, for example, be a triphenyl phosphene ($P(R^C-C_6H_4)_3$) or a trialkyl phosphene ($P(R^C R^{19})$, wherein $R^{19}$ is an alkyl group). $R^C$ is a $CO_2$-philic group as described above. $R^C$ may, for example, be 1H, 1H, 2H, 2H-perfluorooctyl(—$(CH_2)_2(CF_2)_6F$). Preferably, X is Cl.

Use of carbon dioxide as the process solvent ameliorates several engineering and hazardous problems inherent to direct synthesis of hydrogen peroxide from hydrogen and oxygen. For example:

1. The substantially total miscibility of $H_2$ and $O_2$ in carbon dioxide at high pressure eliminates the safety hazard of having a hydrogen and oxygen headspace.
2. The carbon dioxide liquid or supercritical phase surrounding the $H_2$ and $O_2$ molecules acts as heat sink for a potential explosive reaction between $H_2$ and $O_2$.
3. The high dissolving ability of $CO_2$ for $H_2$ and $O_2$ and the $CO_2$-philicity of the $CO_2$-philic functionalized catalyst favors a fast reaction in $CO_2$ between the two components.
4. The low viscosity and low hydrogen peroxide dissolving ability of $CO_2$ provide favorable condition for a fast partitioning of $H_2O_2$ towards the aqueous phase. This minimizes the time contact of $H_2O_2$ with the $CO_2$-philic catalyst and, therefore, the catalytic decomposition of $H_2O_2$. The decomposition of $H_2O_2$ is also minimized by the acidic pH formed at the contact between water and $CO_2$.
5. Use of a small water holdup (that is, the amount of water in the reactor in a bi-phasic system or the water flow rate in the case that a liquid-liquid extraction is carried out) allows formation of high concentration of $H_2O_2$ in the aqueous phase.
6. Replacement of an organic solvent with $CO_2$ eliminates the remediation of $H_2O_2$ aqueous solution due the potential contamination with organic solvents.

Synthesis of a suitable $CO_2$-philic catalysts for use in the present synthesis of hydrogen peroxide from hydrogen and oxygen is described in the Experimental Examples.

EXPERIMENTAL EXAMPLES

Direct Synthesis from Hydrogen and Oxygen
Materials and Procedure
1,4-Dibromobenzene (98%; Aldrich), 1-bromo-4-iodobenzene (98%; Aldrich), magnesium (turnings, 99.98%; Aldrich), perfluorohexyl iodide (99%; Aldrich), 1,1,1,2,2,3,3,4,4,5,5,6,6-tridecafluoro-8-iodooctane (96%; Aldrich), copper (I) chloride (99.995%; Aldrich), phosphorous trichloride (99.9%; Aldrich), tert-butyllithium (1.7 M solution in pentane; Aldrich), trichlorosilane (99%; Aldrich), triethylamine (99.5%; Fluka), bis(acetonitrile)dichloropalladium (II) (99.99%; Aldrich), dichlorobis (triphenylphosphine)palladium(II) (99.99%; Aldrich) were used as received. Reactions involving air- or moisture sensitive materials were performed under argon using Schlenk techniques.

All NMR spectra were recorded on a Bruker DMX300 instrument at the base frequency of 121.49 MHz for $^{31}$P and 300.13 MHz for $^1$H. The samples were prepared in 8 mm NMR tubes placed coaxially in standard, thin-walled, 10 mm tubes containing CDCl$_3$ as chemical shift standard. Chemical shifts were reported in ppm relative to TMS for $^1$H NMR and to 85% H$_3$PO$_4$ for $^{31}$P NMR.

EXAMPLE 1

This example describes the procedure used to synthesize 1-Bromo-4-(Tridecafluorohexyl)benzene (2a) illustrated below. See Bhattacharyya, P.; Gudmunsen, D.; Hope, E. G.; Kemmitt, R. D. W.; Paige, D. R.; Stuart, A. M. Phosphorous (III) Ligands with Fluorous Ponytails. *J. Chem. Soc. Perkin Trans. 1* 1997, 3609.

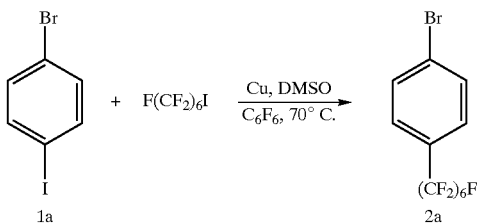

In a typical experiment, a solution of F(CF$_2$)$_6$I (8.92 g, 0.02 mol) in hexafluorobenzene (20 ml) was added dropwise to a mixture of 4-bromoiodobenzene (1a) (5.77 g, 0.02 mol), 2,2'-pypyridine (0.24 g., 1.5 mmol), Cu powder (3.23 g, 0.05 mol), DMSO (20 ml) and hexafluorobenzene (30 ml) at 70° C., under Ar atmosphere. The reaction mixture was stirred for 72 h at 70° C. After filtration of the catalyst and hydrolysis with 100 ml of water, the product was extracted with dichloromethane (100 cm$^3$), and the organic layer was subsequently washed with water, and dried over MgSO$_4$. Then, the product was extracted with perfluoro-1,3-dimethylcyclohexane (3×20 cm$^3$) and the solvent was removed under vacuum. Distillation gave the product as a colorless liquid. (b.p. 45–47° C. at 5 10$^{-3}$ mmHg) (72%). $^1$H NMR (δ, CDCl$_3$, 300 MHz) 7.72 (2H, d, 2,6-ArH), 7.48 (2H, d, 3,5-ArH).

Example 2

This example describes the procedure used to synthesize 1-Bromo-4-(1H, 1H, 2H, 2H-Perfluorooctyl)benzene (2b) illustrated below: See Kainz, S.; Luo, Z. Y.; Curran, D. P.; Leitner, W. Synthesis of Perfluoroalkyl-Substituted Aryl Bromides and Their Purification Over Fluorous Reverse Phase Silica. *Synthesis* 1998, 1425.

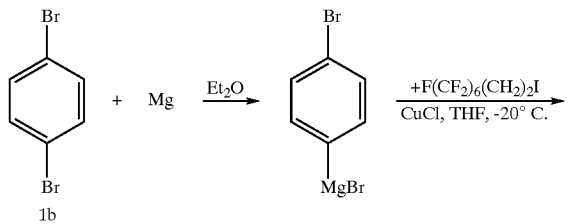

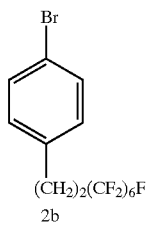

A 100 ml three-neck flask equipped with a dropping funnel and thermometer, previously evacuated and then filled with Ar was charged with Mg turnings (2.07 g, 0.0862 mol) and Et$_2$O (ca 5 ml) such that the solvent fully covered the magnesium particles. A solution of p-dibromobenzene (18.06 g, 0.075 mol) in Et$_2$O (ca 35 ml.) was added dropwise to the reaction mixture slowly enough to maintain a gentle boiling of the solvent. The mixture was subsequently stirred at room temperature overnight. After filtration, the yellowish resulting solution was added dropwise to 1,1,1,2,2,3,3,4,4,5,5,6,6-tridecafluoro-8-iodooctane (31.9 g, 0.0675 mol) and CuCl (0.2 g) in dry tetrahydrofuran (ca 45 ml) over 1 h at −20° C. The slightly yellow reaction mixture was allowed to warm slowly to room temperature in a 4 h period. The mixture was hydrolyzed with 10% aqueous NH$_4$Cl (50 cm$^3$) and the organic layer was collected, washed with water (2×30 cm$^3$), and dried over MgSO$_4$. The solvent was then removed under vacuum affording 19 g of a brown-yellow oil. Distillation gave the product as a colorless liquid (9.5 g (28%); b.p 95–100° C./10$^{-2}$ mmHg). $^1$H NMR (δ, CDCl$_3$, 300 MHz) 7.42 (2H, d, 2,6-ArH), 7.06 (2 H, d, 3,5-ArH), 2.84 (2H, m, H$_2$C$^\alpha$), 2.30 (2H, m, H$_2$C$^\beta$).

Example 3

This example describes the procedure used to synthesize Tris(4-tridecafluorohexylphenyl)phosphine (3a) illustrated below:

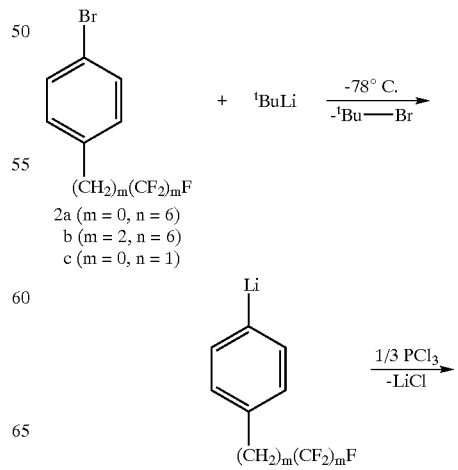

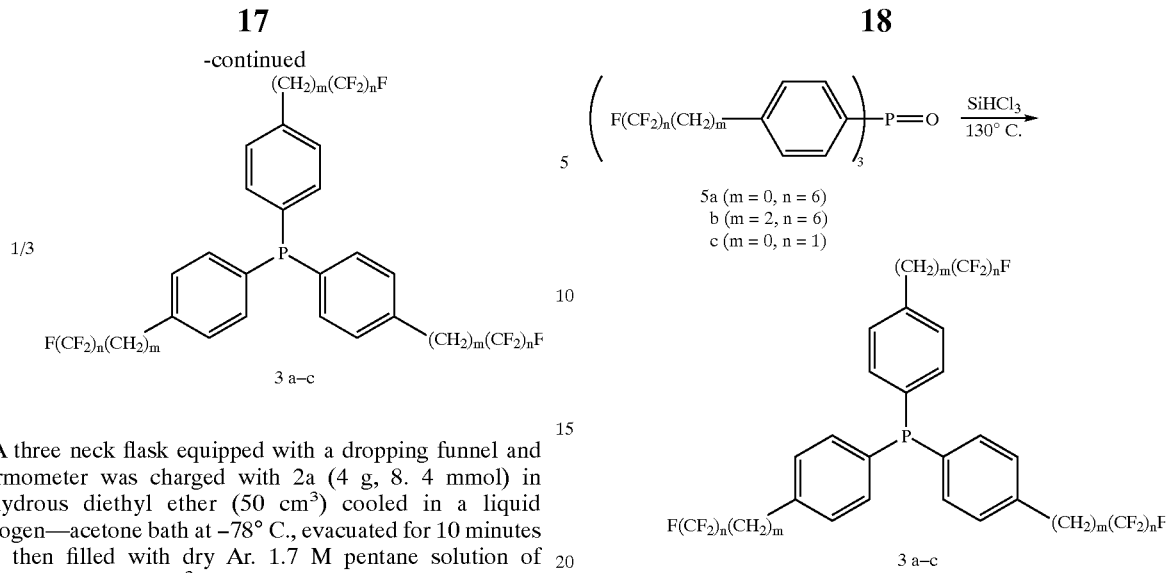

3 a–c

A three neck flask equipped with a dropping funnel and thermometer was charged with 2a (4 g, 8. 4 mmol) in anhydrous diethyl ether (50 cm³) cooled in a liquid nitrogen—acetone bath at −78° C., evacuated for 10 minutes and then filled with dry Ar. 1.7 M pentane solution of 'Butyllithium (9.9 cm³, 0.017 mol) was added dropwise under stirring over 1 h at −78° C., and the slightly yellow resulting mixture was stirred at this temperature for 30 minutes. Subsequently, phosphorous trichloride (0.424 g, 3.1 mmol) in diethyl ether (5 cm³) was added dropwise over 1 h at −78° C., and the reaction mixture was kept at this temperature (−78° C.) for an additional hour and then allowed to warm at room temperature over a 12 h period. After hydrolysis with 10% aqueous $NH_4Cl$ (50 cm³), the organic layer was washed with water and dried over $MgSO_4$. The water phase was washed with diethyl ether (3×20 cm³). The combined organic layers were concentrated to 5 cm³ and then passed through a silica gel column, using a 95% hexane—5% ethylacetate mixture as eluent. Evaporation of the solvent yields 3a as white solid. (2.1 g (53%), m. p. 63° C.). $^1$H NMR (δ, $CDCl_3$, 300 MHz) 7.6 (6H, d, 2,6-ArH), 7.4 (6H, t, 3,5-ArH) $^{31}$P $\{^1H\}$NMR (δ, $CDCl_3$, 121.49 MHz) −5.6.

Example 4

This example describes the procedure used to synthesize Tris(4-(3,3,4,4,5,5,6,6,7,7,8,8,8-tridecafluoro-1-octylphenyl)phosphine (3b). This was prepared by the same method as described in example 3 by using 2b (4.23 g, 8.4 mmol) affording 3b as a white solid (1.8 g (45%), m. p. 58° C.). $^1$H NMR (δ, $CDCl_3$, 300 MHz) 7.3 (6H, d, 2,6-ArH), 7.1 (6H, t, 3,5-ArH), 2.84 (6H, m, $H_2C^\alpha$), 2.30 (6H, m, $H_2C^\beta$). $^-$P$\{^1H\}$NMR (δ, $CDCl_3$, 121.49 MHz) −7.1.

Example 5

This example describes the procedure used to synthesize Tris(4-trifluoromethylphenyl)phosphine (3c). This was prepared by the same method as described in example 3 by using 4-trifluoromethyl-bromobenzene, 2c (1.89 g, 8 mmol) affording 3c as a white solid. (0.79 g (55%), m. p. 70° C.). $^1$H NMR (δ, $CDCl_3$, 300 MHz) 7.6 (6H, d, 2,6-ArH), 7.4 (6H, t, 3,5-ArH). $^{31}$P $\{^1H\}$NMR (δ, $CDCl_3$, 121.49 MHz) −5.3.

Example 6

This example describes the procedure used to reduce tris(4-perfluoroalkylphenyl)phosphine oxide (5), as illustrated below (See Sinou, D.; Pozzi, G.; Hope, E. G.; Stuart, A. M. A Convenient Access to Triarylphosphines with Fluorous Phase Affinity. *Tetrahydron Lett.* 1999, 40, 849):

5a (m = 0, n = 6)
b (m = 2, n = 6)
c (m = 0, n = 1)

3 a–c

Trichlorosilane (0.41 g, 3 mmol) was added dropwise to a mixture of 5a (0.87 g, 0.7 mmol), triethylamine (0.3 g., 3 mmol) and dry toluene (20 ml.). The mixture was refluxed for 3 h at 110° C., cooled to 5° C. and treated with pre-cooled 2N NaOH (25 cm³). The aqueous layer was extracted with diethyl ether (2×15 ml). The organic layer was washed with water until neutral. Evaporation of the solvent yielded phosphine 3a as a white solid. (0.73 g (85%)).

Example 7

This example describes the procedure used to synthesize dichlorobis(tri-(4-tridecafluorohexylphenyl)phosphine)) palladium(II) (4a), as illustrated bellow (See Carroll, M. A.; Holmes, A. B. Palladium-Catalyzed Carbon-Carbon Bond Formation in Supercritical Carbon Dioxide. *Chem Commun.* 1998, 1395):

$P(C_6H_4\text{—}(CH_2)_{\overline{m}}\text{—}(CF_2)_nF)_3$ + $[Pd(MeCN)_2]Cl_2$ $\xrightarrow{CH_2Cl_2}$ 3 a (m = 0, n = 6)
b (m = 2, n = 6)
c (m = 0, n = 1)

4a–c

A solution of 3a (1.3 g, 1 mmol) in chloroform (15 cm³) was mixed with $[Pd(MeCN)_2]Cl_2$ (0.13 g, 0.5 mmol) for 15 minutes. The resulting yellow-orange solution was concentrated, and passed through a silica gel column using a hexane—ethylacetate mixture of increasing polarity as eluent. Evaporation of the solvent from the fractions obtained with 10% ethylacetate—90% hexane mixture gave the product, 4a as yellow solid. (0.79 g, 55%). $^1$H NMR ($\delta$, CDCl$_3$, 300 MHz) 7.6 (12H, d, 2,6-ArH), 7.4 (12H, t, 3,5-ArH). $^{31}$P $\{^1$H$\}$NMR ($\delta$, CDCl$_3$, 121.49 MHz) 23.8.

Example 8

This example describes the procedure used to synthesize dichlorobis(tri-(4-(3,3,4,4,5,5,6,6,7,7,8,8,8-tridecafluoro-1-octyl)phenyl)-phosphine)) palladium(II) (4b). This was prepared by the same method as described in example 7 by using 3b (1.37 g, 1 mmol) affording 4b as yellow solid. (0.91 g, 62%) $^1$H NMR ($\delta$, CDCl$_3$, 300 MHz) 7.6 (12H, d, 2,6-ArH), 7.3 (12H, t, 3,5-ArH), ), 2.9 (6H, m, H$_2$C$^\alpha$), 2.3 (6H, m, H$_2$C$^\beta$) $^{31}$P $\{^1$H$\}$NMR ($\delta$, CDCl$_3$, 121.49 MHz) 22.5.

Example 9

This example describes the procedure used to synthesize dichlorobis(tri-(4-trifluoromethylphenyl)phosphine)) palladium(II) (4c). This was prepared by the same method as described in example 7 by using 3c (0.5 g, 1 mmol) affording 4c as yellow solid. (0.36 g, 62%) $^1$H NMR ($\delta$, CDCl$_3$, 300 MHz) 7.61 (12H, d, 2,6-ArH), 7.4 (12H, t, 3,5-ArH). $^{31}$P $\{^1$H$\}$NMR ($\delta$, CDCl$_3$, 121.49 MHz) 23.9.

Example 10

This example describes the procedure used to synthesize Fluorous Reverse Phase (FRP) (7), as illustrated below (See Curran, D. P.; Hadida, S.; He, M. Thermal Allylations of Aldehydes with a Fluorous Allylstannane, Separation of Organic and Fluorous Products by Solid Phase Extraction with Fluorous Reverse Phase Silica Gel. *J. Org. Chem.* 1997, 62, 6714):

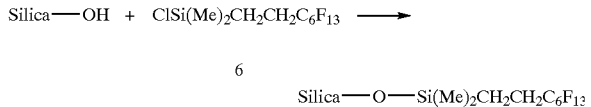

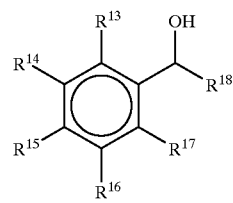

Dimethyl[2-(perfluorohexyl)ethyl]silyl chloride (6) (50.0 g) was added to a mixture of dry toluene, imidazole (9.5 g) and silica gel (Davisil, 35–60 mesh, 99±%) previously dried (120° C., under vacuum, 12 h). The resulting slurry was heated at 100° C. and kept at this temperature for 3 d without stirring. Functionalized silica gel (7) was sequentially washed with toluene, MeOH, MeOH/H$_2$O, THF, Et$_2$O and MeCN in a filtering funnel and then dried under vacuum.

Example 11

The following example provides experimental details for a typical reaction of H$_2$ and O$_2$ over the "CO$_2$-philic" Pd catalysts synthesized as in examples 1–10. Direct reaction of H$_2$ and O$_2$ in liquid CO$_2$ Was conducted in a high-pressure batch reactor at room temperature and P=170 bar. Experimental setup shown in FIG. 1 consists of: (1) 35 cm$^3$ high-pressure batch reactor which walls were previously passivated with 35% HNO$_3$ at 150 F for 2 h to avoid decomposition of H$_2$O$_2$ on the stainless steel, (2) two syringe pumps where H$_2$—CO$_2$ and air-CO$_2$ mixtures were prepared, and (3) two high-pressure HPLC injection valves (Rheodyne) for precise measurement of the amount of air and H$_2$ added to the system.

In a typical experiment, the reactor was charged with deionized water, H$_2$SO$_4$ (96%), Pd-catalyst, and NH$_4$Cl. After 15 minutes evacuation, air was injected into the reactor and one of the syringe pumps (SP1) was charged with hydrogen. The system (SP1 and the reactor) was then pressurized with CO$_2$ (P=135 bar) and the reaction was started by injecting the CO$_2$—H$_2$ mixture into the reactor. After 3 h of reaction (T=25° C., P=170 bar) the system was slowly depressurized, and Pd-catalyst extracted with CDCl$_3$. The aqueous phase was diluted with deionized water and titrated with KMnO$_4$ in the presence of 96% H$_2$SO$_4$.

Example 12

Following the procedure of example 11, a CO$_2$-philic Pd catalyst (4b) made as per example 8 was used to produce H$_2$O$_2$. The reaction vessel was charged with deionized water (3.5 cm$^3$), H$_2$SO$_4$ (96%, 0.04 g, 0.3 mmol), "CO$_2$-philic" Pd catalyst (0.046 g, 0.017 mmol), and NH$_4$Cl (0.0077 g, 0.1 mmol). 31 cm$^3$ of air (P=10.9 bar, 15 mmol) and 2 cm$^3$ (P=6.5 bar, 0.45 mmol) were injected into the reactor. The operating pressure and temperature were 2450 Psi and 25° C. respectively. After 3 h of reaction, H$_2$O$_2$ yield was 43%.

Although the present invention has been described in detail in connection with the above examples, it is to be understood that such detailed is solely for that purpose and that variation can be made by those skilled in the art without departing from the spirit of the invention except as it may be limited by the following claims.

What is claimed is:

1. A method for synthesizing hydrogen peroxide, comprising the steps of:
   mixing an analog of a secondary alcohol that is soluble in or miscible with carbon dioxide with a free radical initiator and oxygen in carbon dioxide to generate hydrogen peroxide.

2. The method of claim 1 wherein the free radical initiator is a peroxide.

3. The method of claim 1 wherein the analog of a secondary alcohol has the formula:

wherein $R^{13}$, $R^{14}$, $R^{15}$, $R^{16}$, and $R^{17}$ are independently, the same or different, H, $R^C$ or $R^SR^C$, wherein $R^S$ is a spacer group and $R^C$ is a CO$_2$-philic group, and wherein at least one member selected from the group consisting of $R^{13}$, $R^{14}$, $R^{15}$, $R^{16}$, and $R^{17}$ is not H, and $R^{18}$ is a methyl group.

4. The method of claim 3 wherein the CO$_2$-philic group comprises a fluoroalkyl group, a fluoroether group, a silicone group, an alkylene oxide group, a fluorinated acrylate group, or a phosphazine group.

5. The method of claim 4 wherein the spacer group is an alkylene group, an amino group, an amido group, an alkyl ester group or an ester group.

6. The method of claim 5 wherein the spacer group is —NHCO—, —NHC$_2$CO— or —CH$_2$OCO—.

7. The method of claim 4 wherein molecular weight of the fluoroalkyl group, the fluoroether group, the silicone group or the alkylene oxide group is between approximately 50 and approximately 7500.

8. The method of claim 4 wherein molecular weight of the fluoroalkyl group, the fluoroether group, the silicone group or the alkylene oxide group is between approximately 500 and approximately 5000.

9. The method of claim 4 wherein molecular weight of the fluoroalkyl group, the fluoroether group, the silicone group or the alkylene oxide group is between approximately 500 and approximately 1500.

10. The method of claim 4 wherein the fluoroalkyl group has the repeat unit:

11. The method of claim 4 wherein the fluoroether group has the repeat unit:

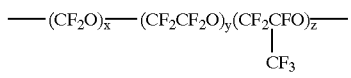

wherein each of y and z is an integer greater than or equal to 0 and at least one of x, y and z is not equal to 0.

12. The method of claim 4 wherein the silicone group has the repeat unit:

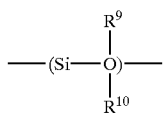

wherein R9 and R10 are, independently, the same or different, H, an alkyl group, an aryl group, an alkenyl group, and an alkoxyl group.

13. The method of claim 12 wherein $R^9$ or $R^{10}$ is a fluoroalkyl group.

14. The method of claim 4 wherein the alkylene oxide group has the repeat unit:

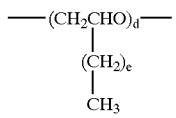

wherein d is an integer and e is an integer.

15. The method of claim 1 wherein the secondary alcohol has the formula R13CH(OH)R18 wherein R13 is a CO2-philic group and R18 is an alkyl group.

16. The method of claim 15 wherein the CO2-philic group comprises a fluoroalkyl group, a fluoroether group, a silicone group, an alkylene oxide group, a fluorinated acrylate group, or a phosphazine group.

17. The method of claim 1 wherein a reaction of the analog of the secondary alcohol with the free radical initiator and oxygen takes place in the presence of a catalyst.

18. The method of claim 17 wherein the catalyst is miscible with or soluble in carbon dioxide.

19. The method of claim 18 wherein the catalyst has the formula:

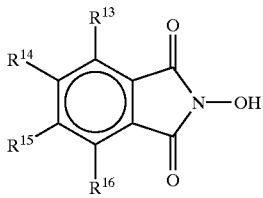

wherein $R^{13}$, $R^{14}$, $R^{15}$ and $R^{16}$, are independently, the same or different, H, RC or RSRC, wherein RS is a spacer group and RC is a $CO_2$-philic group.

20. The method claim 19 wherein at least one member selected from the group consisting of $R^{13}$, $R^{14}$, $R^{15}$ and $R^{16}$ is not H.

21. The method of claim 20 wherein the $CO_2$-philic group is selected from the group consisting of a fluoroalkyl group, a fluoroether group, a silicone group, an alkylene oxide group, a fluorinated acrylate group, and a phosaphazine group.

22. The method of claim 1 wherein the hydrogen peroxide is recovered via extraction into an aqueous phase.

23. The method of claim 1 wherein a ketone produced in the reaction to form hydrogen peroxide is hydrogenated to regenerate the analog of the secondary alcohol.

* * * * *